United States Patent [19]

Lancaster et al.

[11] Patent Number: 5,057,411

[45] Date of Patent: Oct. 15, 1991

[54] TYPE-SPECIFIC PAPILLOMAVIRUS DNA SEQUENCES AND PEPTIDES

[75] Inventors: Wayne D. Lancaster; A. Bennett Jenson, both of Rockville, Md.

[73] Assignee: Georgetown University, Washington, D.C.

[21] Appl. No.: 346,283

[22] Filed: May 1, 1989

Related U.S. Application Data

[63] Continuation of Ser. No. 719,979, Apr. 4, 1985, abandoned.

[51] Int. Cl.$^5$ ............................................. C12Q 1/68
[52] U.S. Cl. ........................................ 435/6; 435/5; 436/501; 436/811; 536/27; 935/78
[58] Field of Search ................. 435/5, 6; 536/27; 436/501, 811; 935/78

[56] References Cited

U.S. PATENT DOCUMENTS

| | | |
|---|---|---|
| 4,190,645 | 2/1980 | Almeida . |
| 4,358,535 | 11/1982 | Falkow et al. ............... 435/35 X |
| 4,419,446 | 12/1983 | Howley et al. .............. 935/78 X |
| 4,551,270 | 11/1985 | Danos et al. . |

FOREIGN PATENT DOCUMENTS

| | | |
|---|---|---|
| 92456 | 10/1983 | European Pat. Off. . |
| 133123 | 2/1985 | European Pat. Off. . |
| 192001 | 8/1986 | European Pat. Off. . |

OTHER PUBLICATIONS

Groff, D. E. et al., *J. Virology*, vol. 56, Oct. 1985, pp. 85-91.

*Chemical Abstracts*, vol. 106, No. 25, issued 6/22/87, p. 348, abst. No. 210547s, Orth, G. et al., "Papilloma Virus . . . Virus Infections."

*Chemical Abstracts*, vol. 99, No. 23, issued 12/5/83, p. 218, abst. No. 188882k, Lancaster, W. D. et al., "Human Papillomavirus: . . . Cervix."

Lass, J. H. et al., Am. J. Ophthal 96, 1983, pp. 670-674.
Lancaster, W. D. et al., Intervirology 20, 1983, pp. 202-212.

Howley, P. M. et al (Organizer), J. Cell. Biochem. Suppl 9C, 1985, pp. 65-100.

Danos O. et al., Embo J. 1:231-6 (1982), Human PV la complete DNA sequence.

Schwarz, E. et al., Embo J. 2:2341-8 (1983), DNA sequence and genome organization of genital human PV type 6b.

Jenson, A. B. et al., J. Nat'l Cancer Society 64:495-500 (1980), Immunology relatedness of PVs from different species.

Chen, E. Y. et al., Nature 299: 529-33 (1982), Primary structure and genetic organization of the bovine papillomavirus type 1 Genome.

Law, M. F. et al., J. Virology 32:199-207 (1979), Conserved polynucleotide sequence among genomes of papillomaviruses.

Heilman, C. A. et al., J. Virology 36:395-497 (1980), Cloning of human papillomavirus genomic DNAs and analysis of homologous polynucleotide sequence.

Howley P. et al., Cold Spg. Har. Conf. Cell Prolif. 7:233-47 (1980), Molecular characterization of PV genomes.

Lancaster W. et al., Cold Spg. Har. Conf. Cell Prolif. 7:223-32 (1980), State of bovine PV DNA in connective tissue tumors.

Lancaster W. et al., Virology 89:372-9 (1978), Demonstration of two distinct classes of bovine PVs.

(List continued on next page.)

*Primary Examiner*—Amelia Burgess Yarbrough
*Attorney, Agent, or Firm*—Sterne, Kessler, Goldstein & Fox

[57] ABSTRACT

The polynucleotide sequence fragment conferring immunologic specificity to papillomavirus (PV) has been located and isolated. From this information, assays for type-specific PV, including DNA probes, RNA probes, immunoassays and the like are produced. The vaccines against specific PVs may be produced also.

Further, the genus-specific amino acid sequence of the L1 capsid protein has been identified.

28 Claims, 9 Drawing Sheets

OTHER PUBLICATIONS

Lack E. et al., Intervirology 14: 148–54 (1980), Immunoperoxidase localization of human PV, Laryngeal papillomas.

Von Krogh G. Intn'l J. Derm. 18:195–204 (1979), Warts: Immunologic factors of prognostic significance.

Kryzek R. et al., J. Virology 36:236–44 (1980), Anogenital warts contain several distinct species of human warts.

Costa J. et al., Amer. J. Clin. Pathol. 75: 194–7 (1981), Human PV antigens in juvenile multiple laryngeal papilloma.

Morin C. et al., J. National Cancer Inst. 66:831–5 (1981), PV etiology of condylomas cervix lesions.

Lancaster W. et al., Intervirology 15: 204–212 (1981), PV genus-specific antigens and DNA in laryngeal papilloma.

Staquet M. et al., Dermatologica 162: 213–219 (1981), Human PV type 1 purified from human genital warts.

Kurman R. et al., Amer. J. Obstet. Gynecol. 140:931–5 (1981), Immunoperoxidase localization of PV antigens in cervical dysplasia and vulvar condylomas.

Lancaster, W. D., Virology 108: 251–5 (1981), Lack of integration of bovine PV DNA in virus-induced equine and bovine tumor cells and virus transformed cells.

Pass F. et al., J. Investigat. Dermatol. 60:307–11 (1973), Wart associated antigens. II human immunity to viral structural proteins.

Silpananta P. et al., JRCS Med., Sci. 3:517–8 (1985), Chromatographic studies of soluble proteins from human and bovine wart tissue.

Meinke W. et al., J. Gen. Virology 52:15–24 (1981), Isolation and characterization of the major capsid protein of bovine PV type 1.

Pfister H. et al., Rev. Physiol Biochem. Pharm. 99 111–181 (1983), Biolog. and Biochem. of PVs.

Moar M. et al., J. Virology 39:945–9 (1981), Unintegrated viral DNA sequence in hamster tumor induced by bovine PV.

Howley, P. Arch. Pathol. Lab. Med. 106: 429–32 (1982), The human PVs.

Lee K. et al., Cancer Res. 29:1393–7 (1969), Precipitin response of cattle to bovine PV.

Lee K. et al., J. Invest Dermat. 52: 45414 64 (1969), Histochem. studies exp'tlly produced bovine fibropapillomas.

Tagami H. et al., Brit. J. Derm. 90:147–54 (1974), Regression of plantar warts following spontaneous inflammation.

Berman, A. et al., Brit. J. Dermatol. 99:179–182 (1978),. Efflorescence of nNew wWarts:sign of onset of involution in flat warts.

Barthold, S. W. et al., J. Am. Vet. Med. Assoc'n, 165:276–80 (1974), Atypical warts in cattle.

Supplementary European Search Report for EP 86 90 2614.

Kremsdorf et al., *J. Virology* 52:1013–1018 (1984).

Chow, L. T. et al., in *Cancer Cells 5/Papillomaviruses*, B. M. Steinberg et al., eds., 1987, Cold Spring Harbor Laboratory, New York, pp. 55–72.

```
BPV-1    MALWQQGQKLYLPPTPVSKVLCSETYVQRKSIFYHAETERKKTIGH          46
DPV      MAFWQPGQALYLPPTPVTKVLCSEQYINVRDIFYHGETERMLTSGS          46

BPV-1    PYYPVSIGAK TVPKVSANQYRVFKIQLPDPNQFALPDRTVHNPSKERLVW      96
DPV      ILSLEVTQKHTTVPKVSPNQYRVFRVAKPDPNQFALPDKALHNPSKERLVW     97

BPV-1    AVIGVQVSRGQPLGGTVTGHPTFNALLDAENVNRKVTTQTTDDRKQTGLD       146
DPV      AVVGVQVSRGQPLGGEVRGHSYFNTFLDAENVSKKVTAQGTDDRKQAGMD       147

BPV-1    AKQQQILLLGCTPAEGEYWTTARPCVTDRLENGACPPLELKNKHIEDGDM       196
DPV      TKQQQVLMLGCTPAIGEYWTKARPCVTDRPDAGSCPPIELKLSFIEDGDM       197

BPV-1    MEIGFGAANFKEINASKSDLPLDIQNEICLYPDYLKMAEDAAGNSMFFFA       246
DPV      MDIGFGAANFKELNATKSDLPLDIANSICLYPDYLKMTEEAAGNSMFFFA       247

BPV-1    RKEQVYVRHIWTRGGSEKQAPTTDFYLKNNKGDATLKIPSVHFGSPSGSL       296
DPV      RKEQVYVRHIWTPWGTDKELPPEAYYLK PPGEMELKMPSVFFSSPSGSL       296

BPV-1    VSTDNQIFNRPYWLFRAQGMNNGIAWNNLLFLTVGDNTRGTNLTISVASD       346
DPV      VSTDGQLFNRPYWILRAQGMNNGVCWNNTLFVTVGDNTRGSTLTITVPNN       346

BPV-1    GTPLTEYDSSKFNVYHRHMEEYKLAFILELCSVEITAQTVSHLQGLMPSV       396
DPV      DSPLTEYDTSKFNVYQRHVEEFKLAFILELCSVELTPSTVSSLQGSMPSI       396

BPV-1    LENWEIGVQPPTSSILEDTYRYIESPATKCASNVIPAK EDPYAGFKFWNI     446
DPV      LENWEINLQPPTSSVLEDIYRFIDSPATKCADNVSPSKPEDPYSAHKFWST     447

BPV-1    DLKEKLSLDLDQFPLGRRFLAQQGAGCSTVRKRRISQKTSSKPAKKKKK        495
DPV      NLKEKLSLDLDQFPLGRLVLQFDCRLHRLLPQKDHFTYPEKRYKRHMRI        496

BPV-1
DPV      TGTVRKVLLYICFSLN                                         512
```

FIGURE 2

```
BPV-2      MALWQQ------------------------------------------
BPV-1      MALWQQGQKLYLPPTPVSKVLCSETYVQRKSIFYHAETERKKTIGH        46
DPV        MAFWQPGQALYLPPTPVTKVLCSEQYINVRDIFYHGETERMLTSGS        46

BPV-2      ------------------------------------------------
BPV-1      PYYPVSIGAK TVPKVSANQYRVFKIQLPDPNQFALPDRTVHNPSKERLVW   96
DPV        ILSLEVTQKHTTVPKVSPNQYRVFRVAKPDPNQFALPDKALHNPSKERLVW   97

BPV-2      ------------------------------------------------
BPV-1      AVIGVQVSRGQPLGGTVTGHPTFNALLDAENVNRKVTTQTTDDRKQTGLD   146
DPV        AVVGVQVSRGQPLGGEVRGHSYFNTFLDAENVSKKVTAQGTDDRKQAGMD   147

BPV-2      DKQQQILLLGCTPAEGEYWTTARPCVTDRLENGACPPLELKNKHIEDGDM
BPV-1      AKQQQILLLGCTPAEGEYWTTARPCVTDRLENGACPPLELKNKHIEDGDM   196
DPV        TKQQQVLMLGCTPAIGEYWTKARPCVTDRPDAGSCPPIELKLSFIEDGDM   197

BPV-2      MEIGFGAANFKTLNASKSDLPLDIQNEICLYPDYLKMAQDAAGNSMFFFA
BPV-1      METGFGAANFKEINASKSDLPLDIQNEICLYPDYLKMAEDAAGNSMFFFA   246
DPV        MDTGFGAANFKELNATKSDLPLDIANSICLYPDYLKMTEEAAGNSMFFFA   247

BPV-2      RKEQVYVRHIWTRGGSEKsAPsKDFYLKNgRGsETLKIPSVHFGSPSGSL
BPV-1      RKEQVYVRHIWTRGGSEKQAPTTDFYLKNNKGDATLKIPSVHFGSPSGSL   296
DPV        RKEQVYVRHIWTPWGTDKELPPEAYYLK PPGEMELKMPSVFFSSPSGSL   296

BPV-2      VSTDNQIFNRPYWLFRAQGMNNGIAWNNLLFLTVGDNTRGTNLsISVAsD
BPV-1      VSTDNQIFNRPYWLFRAQGMNNGIAWNNLLFLTVGDNTRGTNLTISVASD   346
DPV        VSTDGQLFNRPYWILRAQGMNNGVCWNNTLFVTVGDNTRGSTLTITVPNN   346

BPV-2      GTPLsEYDTGKFNLYHRHMEEYKLAFILELCFVE----------------
BPV-1      GTPLTEYDSSKFNVYHRHMEEYKLAFILELCSVEITAQTVSHLQGLMPSV   396
DPV        DSPLTEYDTSKFNVYQRHVEEFKLAFILELCSVELTPSTVSSLQGSMPSI   396

BPV-2      ------------------------------------------------
BPV-1      LENWEIGVQPPTSSILEDTYRYIESPATKCASNVIPAK EDPYAGFKFWNI  446
DPV        LENWEINLQPPTSSVLEDIYRFTDSPATKCADNVSPSKPEDPYSAHKFWST  447

BPV-2      --RDKLSLDLDQFPLGRRFLAQQGAGCSAVRKRAvATKNSSKPAKRKK
BPV-1      DLKEKLSLDLDQFPLGRRFLAQQGAGCSTVRKRRISQKTSSKPAKKKKK   495
DPV        NLKEKLSLDLDQFPLGRLVLQFDCRLHRLLPQKDHFTYPEKRYKRHMRI   496

BPV-2      
BPV-1      
DPV        TGTVRKVLLYICFSLN                                   512
```

FIGURE 3

```
BPV-1      MALWQQGQ KLYLPPTPVSKVLCSEtYVQRKsIFYHAETERKKTIGH        46
DPV        MAFWQPGQ ALYLPPTPVTKVLCSEQYINVRDIFYHGETERMLTSGS        46
HPV-1A MYNVFQMAVCLPSQNKFYLPPQPITRMVSTDEYVTRTNLFYHATSERLLLVGH      53
CRPV       MAVWLSTQNKFYLPPQPVTKIPSSHEYVTRTNvFYYASSDRLLTVGH        47
HPV-6B     MWRR SDSTVYVPPPNPVSKVVSTDAYVTRTNIFYHASSsRVVAVGH        46
BPV-2      MALWQQ-------------------------------------------
           +----------++-+----------+-------++------+----+-

BPV-1      PYYPvSIGAK TVPKVSANQYRVFKIQLPDPNQFALPDRTVHNPSKERLVW       96
DPV        ILSLEVTQKHTTVPKVSPNQYRVFRVSKPDPNQFALPDKALHNPSKERLVW       97
HPV-1A     PLFEISSNQTVTIPKVSPNEFRVFRVRFADPNRFAFGDKAIFNPETERLVW      104
CRPV       PYYEIRDKGTMLVPKVSPNQTRVFRIKLPDPNKFAFGDKQLYDPEKERLVW       98
HPV-6B     PYFsIKRANKTVVPKPSGYQYRVFKVvLPDPNKFALPDsSLFDPTTQRLVW       97
BPV-2      ---------------------------------------------------
           ------     ----++-+----+++-- --+++-++--+-----+---+++

BPV-1      AVIGVQVSRGQPLGGTVTGHPTFNALLDAENV NRKVTTQTT DDRKQTGLD      146
DPV        AVvGVQVSRGQPLGGEVRGHSYFNTFLDAENV SKKVTAQGT DDRKQAGMD      147
HPV-1A     GLRGIEIGRGQPLGIGITGHPLLNKLDDAENPTNYINTHANG DCRQNTAFD      156
CRPV       CLRGIEVNRGQPLGVSVTGNPIFNKFDDVENPTKYYNNHADQQDYRKAMAFD      150
HPV-6B     ACTGIEVSRGQPLGVGVsGHPFLNKYDDVENSGSSGGNPGQ DNRVNVVGMD      147
BPV-2      ----------------------------------------------------
               ---+----+++++----+--  -+----+-++-------- - ------+
                           A

BPV-1      AKQQQILLLGCTPAEGEYWTTARPCVTDRLENGACPPLELKNKHIEDGDM       196
DPV        TKQQQvLMLGCTPAiGEYWTKARPCVTDRPDAGsCPPIELKLSFIEDGDM       197
HPV-1A     AKQTQMFLVGCTPAsGEHWTSSR CPGEQVKLGDCPRVQMISSVIEDGDM       205
CRPV       PKQTQLLMVGCvPATGEHWAQAKQCSADPPQQTDCPPIELVNTVIEDGDM       200
HPV-6B     YKQTQLCMVGCAPPLGEHWGKGKQCTNTPVQAGDCPPLELITSVIQDGDM       197
BPV-2      DKQQQILLLGCTPAEGEYWTTARPCVTDRLENGACPPLELKNKHIEDGDM
           -++-+----++-+---++-+-----+----------++---------+-+++
                                                          B

BPV-1      MEIGFGAANFKEINASKSDLPLDIQNEICLYPDYLKMAEDAAGNSMFFFA        246
DPV        MDIGFGAANFKELNATKSDLPLDIANSICLYPDYLKMTEEAAGNSMFFFA        247
HPV-1A     MHIGFGANDFASLQQDKSDVPLDVvQATCKYPDYIRHNHEAYGNSIFFFA        255
CRPV       CEIGFGAMDHKTLQASLSEVPLELAQSIsKYPDYVKMQKDQFGDSMFFYA        250
HPV-6B     VDTGFGAMNFADLQTNKSDVPIDICGTTCKYPDYLQMASDPYGDRLFFFL        247
BPV-2      MEIGFGAANFKTLNASKSDLPLDIQNEICLYPDYLKMAQDAAGNSMFFFA
           ---+++++---------+--+------+----+++--+-----+---++--
                C                   D
```

FIGURE 4

```
                            TS
        |------------------------------------------|
        |       |--------------------------|       |
BPV-1   RKEQVYVRHIWTRGGSEKQAPTTDF    YLKNnKGDATLKIPSVHFGSPSGSL    296
DPV     RKEQVYVRHIWTPWGTDKELPPEA    YYLK PPGEMELKMPSVFFSSPSGSL    296
HPV-1A  RREQMYTRHFFTRGGSLGDKEAVPQSL YLTSDAEPRTTLATTNYVGTPSGSM    308
CRPV    IREQMYARHFFSRAGGDKENVKSRSYIKRTQMQGEANENIATDNYCITPSGSL    304
HPV-6B  RKEQMFARHFFNRAGEVGEPVPDTLIIKGS   GNRTSVGSSIYVNTPSGSL    295
BPV-2   RKEQVYVRHIWTRGGSEKSAPsKDF    YLKNgRGEETLKIPSVHFGSPSGSL    295
        --++---++-------+------ -- ------ -- ------------+++-
                                                        E
BPV-1   VSTDNQIFNRPYWLFRAQGMNNGIAWNNLLFLTVGDNTRGTNLTISVASD    346
DPV     VSTDgQLFNRPYWILRAQGMNNGVCWNNTLFVTVGDNTRGsTLTITVPNN    346
HPV-1A  VSSDvQLFNRsYWLQRCQGQNNGICWRNQLFITVGDNTRGTsLSISMkNN    358
CRPV    VSSDsQvFNRAYWLQKAQGMNNGVCWDNQIFVTVVDNTRGTILSLVTPSK    354
HPV-6B  VSSEAQLFNKPYWLQKAQGHNNGICWGNQLFVTVVDTTRSTNMTLCSSVT    345
BPV-2   VSTDNQIFNRPYWLFRAQGMNNGIAWNNLLFLTVGDNTRGTNLSISVASD    345
        ++---+-++--++----++--+-+++--+-+---+--++-+-++------

BPV-1   GTPLTEYDS SKFNVYHRHMEEYKLAFILELCSVEITAqTVSHLQGLMPSV    396
DPV     DsPLTEYDT SKFNVYQRHVEEFKLAFILELCSVELTPETVSSLQGSMPS I   396
HPV-1A  STTTYSN AN FNDFLRHTEEFDLsFIVQLCKVKLTPENLAYIHTMDPNI    406
CRPV    EQIKKTHGKTVHFSSYLRHVEEYSLQFvLQLCKVKLTPENLSYLHsMHPTI   404
HPV-6B  TASTYTNSDYKE YMRHVEEYDLQFIFQLCSITLSAEVMAYIHTMNPSV    403
BPV-2   GTPLSEYDT GKFNLYHRHMEEYKLAFILELCFVE----------------
        --------- -------++-++-+-+---+-++----

BPV-1   LENWEIGV QPPTSSILEDTYRYIESPAT KCASNVIPAK EDPYAGFKFWNI   446
DPV     LENWEINL QPPTSSvLEDIYRFIDSPAT KCADNVSPSKP EDPYSAHKFWEV   447
HPV-1A  LEDWQLSVSQPPT NPLEDQYRFLGSSLAAKCPQQAPPEPQQTDPYSQYKFWEV   459
CRPV    IDNWQLSVSAQP SGTLEDQYRYLGSIAT KCP PPAPPKENTDPYKNYKFWEV   455
HPV-6B  LEDWNFGLSPPPN GTLEDTYRYVGSQAITCQKPTPTPEKEKPDPYKNLSFWEV   456
BPV-2   -----------------------------------------------------
        ---+---------+-----++--++---+--- ---+---- -+++-----++--

BPV-1   DLKEKLSLDLDQFPLGRRFLAQQGAGCSTVRKRR ISQKTSSKPAKKKKK_     495
DPV     NLKEKLSLDLDQFPLGRLVLQFDCRLHRLLPQKDHFTYPEKRYKRHMRIT     497
HPV-1A  DvTERMSEQLDQFPLGRKFLYQSGMTERTSTSSTTKRKTVRVSTsAKRRR     497
CRPV    DLsEKLSDQLDQYPLGRKFLNQSGLQRIGTKRPAPAPVSIVKSSKRKRRT     505
HPV-6B  NLKEKFSSELDQYPLGRKFLLQSGYRGRSSIRTGVKRPAVSKASAAPKRK     506
BPV-2   --RDKLSLDLDQFPLGRRFLAQQGAGCSAVRKRAVATKnSSKPAKRKK
        -------+--+++-++++---+--------------------------

BPV-1
DPV     GTVRKVLLYICFSLN                                512
HPV-1A  KA                                             499
CRPV
HPV-6B  RAkTKR                                         512
BPV-2
           - -
```

FIGURE 4

TYPE-SPECIFIC PAPILLOMAVIRUS DNA SEQUENCES AND PEPTIDES

This application is a continuation of application Ser. No. 719,797, filed Apr. 4, 1985, now abandoned.

BACKGROUND OF THE INVENTION

1. Field of the Invention

This invention is directed to the discovery that, within the polynucleotide sequence of papillomavirus (PV), there occur segments of nucleotide sequences which are useful in distinguishing and differentiating between PV types and species. These regions within the genome, the variable regions, are specific to the particular PV type and form the basis for production of DNA probes, antibodies (labelled and unlabelled), polypeptide segments, labelled polypeptide segments, and vaccines which are specific for a given particular PV.

In another aspect of the present invention, it has also been discovered that the polynucleotide sequence of all PVs contains a highly conserved region that is characteristic of all PVs and forms the basis for production of antibodies (labelled and unlabelled) and polypeptide segments (labelled and unlabelled), which are PV genus-specific, i.e. recognize and distinguish any PV and differentiate over non-PV viruses and viral products. This latter DNA sequence is termed "genus specific".

2. Description of the Background Art

The search for a virus involved in the induction of human cancer has been frustrating. A number of viruses have gained renewed interest as possible human cancer viruses; one such virus is the human papillomavirus (HPV). Although HPV was one of the first viruses to be visualized by the electron microscope, little information was available on the biology of the virus until recently. Early studies failed to provide direct indication that HPV may be associated with malignancy (these studies have been reviewed by Roson et al., *Bacteriol. Rev.*, 31: 110–131 (1976)). However, as early as the 1930's, experimental evidence indicated that the cottontail rabbit papillomavirus (CRPV) was oncogenic in its host species (Rous et al., *J. Exp. Med.*, 65: 523–548 (1935)). Further, other animal papillomaviruses have been shown to produce tumors in laboratory animals and some have been shown to be capable of morphologic transformation of cells in culture (Olson et al., *Arch. Environ. Health*, 19: 827–837 (1969)). However, neither experimental transmission of HPV to laboratory animals nor a tissue culture system permissive for virus replication or expression of biological activity has been successful. Accordingly, research on HPV has been limited to, for the most part, physical and chemical characterization of virions obtained from papillomas.

The inability to define a system permissive for replication of HPV virus in culture has been circumvented to some extent by molecular cloning of viral DNA sequences which permit detailed molecular analysis. Further, multiple, minimally related virus types with anatomic site preference have been discovered and HPV antigens and DNA in lesions with malignant potential have been detected. Previously, the causes of these lesions have been attributed to other infectious agents or some other unknown etiology. These developments have rendered the study of HPV attractive from the standpoint of viral oncogenesis.

It is known that the members of the papillomavirus genus are small (50–55 nm diameter), unenveloped viruses with an icosahedral symmetry. Their genome consists of a circular double-stranded DNA molecule containing about 8,000 base pairs (8 kb). The virions may be easily isolated from papillomas which are virus-positive by electron microscopy, by mechanically disrupting the epithelium followed by a series of differential centrifugation steps and banding in cesium chloride. In most preparations, two bands may be visualized, one at 1.33 gm/ml and the other at 1.29 gm/ml. It is believed that the former represents "full" virions which contain DNA, while the latter is composed of "empty" virus shells. The DNA may be isolated by rupture of virions with ionic detergent and removal of protein by organic extraction. The resultant DNA preparation generally contains two forms of DNA, a supercoiled fraction (Fo I) and a nicked-circular form (Fo II).

Five different viruses have been identified that infect cattle, i.e. the bovine papillomaviruses (BPV). These viruses have different degrees of DNA sequence homology, antigenic relatedness, tissue specificity (cutaneous or mucosal surfaces), and induce different types of lesions (fibropapillomas or papillomas).

The human papilloma viruses show even greater diversity. Eighteen different HPV types have now been described in the literature, and it is anticipated that additional types will be discovered. To be classified as a new virus type, there cannot be more than 50% DNA sequence homology under standard conditions of hybridization to previously typed viruses; a virus DNA which hybridizes to greater than 50% sequence homology to a given virus type is considered a subtype (Coggin et al., *Cancer Res.*, 39: 545–546 (1979)). Standard hybridizations are run 25° C. below the melting temperature of the DNAs (Tm-25° C.) which allows for about 17% base mismatch (Laird et al., *Nature*, 224: 149–154 (1969)).

It now appears that the HPVs may be grouped with respect to sequence homology and site of infection as set out in the following Table 1.

TABLE 1

| The Human Papillomaviruses (HPV) | | |
|---|---|---|
| SITE | LESION | % HOMOLOGY WITHIN GROUP |
| CUTANEOUS | | |
| HPV-1 | Plantar Wart | <1% |
| HPV-2 | Common Wart | |
| HPV-4 | Plantar Wart | |
| HPV-7 | Butchers' Common Wart | |
| HPV-3 | Flat Wart | <35% |
| HPV-10 | Flat Wart | |
| HPV-5 | EV* | 5 to 39% |
| HPV-8 | EV | |
| HPV-12 | EV | |
| HPV-14 | EV | |
| HPV-9 | EV | 5 to 19% |
| HPV-15 | EV | |
| HPV-17 | EV | |
| MUCOCUTANEOUS/MUCOSAL | | |
| HPV-6 | Genital Wart | 3 to 25% |
| HPV-11 | Laryngeal Papilloma | |
| HPV-13 | Focal Epithelial Hyperplasia | |
| HPV-16 | Cervical Carcinoma | <1% |
| HPV-18 | Cervical Carcinoma | |

*Pityriasis-like lesions of *epidermodysplasia verruciformis*

Viruses infecting cutaneous surfaces are more likely to have some degree of homology to other HPVs infecting the skin than those infecting mucosal surfaces. Further, although a particular virus type is preferentially associated with a given lesion, it may, on occasion, be found in other lesions. As reported by Jensen et al., *Lab. Invest.*, 47: 491-497 (1982), HPV-1 is associated with about 85% of plantar warts but HPV-2 has also been detected in a small percentage of plantar warts and vice versa. Of special interest is a group of human papillomaviruses, the types 3, 5, 8-10, 12-15, and 17. These viruses are found to be associated with individuals with epidermodysplasia verruciformis (EV), a rare recessive disorder characterized by generalized pityriasis-like lesions or flat warts (Jablonska et al., *Cancer Res.*, 32: 583-589 (1972)). With the exception of types 3 and 10, this group of HPVs have not been detected in warts from healthy individuals, having only been identified in lesions from immunosuppressed renal allograft recipients (Lutzner et al., *J. Invest. Dermatol.*, 75: 353-356 (1980)). It has also been reported that lesions containing HPV-5 and HPV-8 frequently undergo malignant conversion when present on sun-exposed areas. Hybridization analysis of primary and metastatic cancers have shown the presence of HPV-5 and HPV-8 DNA sequences within these tumors (Orth et al., *Cell Prolif.*, 7: 259-282 (1980); Ostrow et al., *Proc. Natl. Acad. Sci.*, 79: 1634-1638 (1982); and Pfister et al., *Rev. Physiol. Biochem. Pharmacol.*, 99: 111-181 (1983)).

Recent studies using nonstringent hybridization conditions have demonstrated that DNA sequences are conserved among the genomes of each HPV genome as well as between HPVs and other animal papillomaviruses (Heilman, C. A., *J. Virol.*, 36: 395-407 (1980); and Law, M. F., *J. Virol.*, 32: 199-207 (1979)). Thus, it is now possible to use a PV-specific DNA probe to examine the DNA prepared from a putative PV-induced lesion to search for related sequences by using nonstringent hybridization conditions. This approach has been demonstrated to be successful for HPV DNA sequences of unknown HPV types as well as in the DNA prepared from anogenital warts (Krzyzek, R. A. et al., *J. Virol*, 36: 236-244 (1980)) and from juvenile laryngeal papillomas (Lancaster, W. D., *Intervirology*, 15: 204-212 (1981)).

In spite of the absence of a suitable tissue culture system for analysis of PV genomes, considerable insight into the possible functions of the virus genomes has been developed as a result of DNA sequence analysis, substantial quantities of the DNA being produced by molecular cloning techniques. The nucleotide sequences for bovine papillomavirus type 1 (BPV-1) (Chen et al., *Nature*, 299: 529-534 (1982)), HPV-1a (Danos et al., *Embo. J.*, 1: 231-236 (1982)), and HPV-6b (Schwartz et al., *Embo. J.*, 2: 2341-2348 (1983)) are now known. Known as well are the DNA sequences for HPV-11, HPV-16, and deer papillomavirus (DPV).

It has also been demonstrated that the papilloma viruses are related antigenically. Although antisera raised against intact viral particles of a specific HPV are type specific and will not react in tissues infected by another HPV type, antisera raised against PV virions that have been disrupted by heat and detergent will cross-react with capsid antigens of all HPVs, as well as PVs of other animal species (Jensen, A. B. et al., *JNCI*, 64: 495-500 (1980)). This information has led to the speculation that there are conserved amino acid sequences in the major capsid proteins of papillomas viruses that are responsible for this genus-specific antigenic cross-reactivity, and that these conserved amino acid sequences are not exposed on the surface of the virion particles (Howley, P. M., *Arch. Pathol. Lab. Med.*, 106: 429-432 (1982)).

The use of antisera raised against the common PV antigens, then, is useful for identification of cells that are productively infected by any HPV, known or unknown. This cross-reacting antisera has allowed pathologists and clinical investigators to identify HPVs as the etiologic agent of juvenile laryngeal papillomatosis (Costa, J. et al., *Am. J. Clin. Pathol*, 75: 194-197 (1981); and Lack, E. et al., *Intervirology*, 14: 148-156 (1981)) and of cervical flat warts (Kurman, R. J. et al., *Am. J. Obstet. Gynecol.*, 140: 931-935 (1981); and Morin, C. et al., *JNCI*, 66: 831-835 (1981)). However, the antisera are not useful or suitable for identifying a specific HPV. Additionally, it is essential that the viral infectivity has progressed to the point that protein expression has occurred, the antisera not being useful for picking up early stages of infectivity or infectivity where protein expression has not occurred.

To date, little is known about the functional aspects of HPV genomes. More information is available regarding animal papillomavirus systems. Because the genomic organization is highly conserved among the papillomaviruses, it is reasonable to assume similar relationships with respect to genome structure and function between animal and human papillomaviruses. Since some of the animal papillomaviruses are highly oncogenic, it is likely that all or a portion of this function may be a property of some of the HPVs as well. Many HPV-induced lesions such as common warts, plantar warts, and flat warts are entirely benign and not clinically associated with progression to carcinomas. However, several HPVs are occasionally associated with subsequent development into squamous cell carcinomas, and HPV-5 has been associated with cutaneous carcinomas in patients with epidermodysplasia verruciformis. Juvenile laryngeal papillomatosis is caused by papillomavirus HPV-11. Rare cases of spontaneous progression to invasive squamosal carcinoma of the larynx in the absence of irradiation have been described by Runckel, D. et al., *Am. J. Surg. Pathol.*, 4: 293-296 (1980). More frequently, following radiation therapy, progression of juvenile laryngeal papillomatosis progresses to squamous cell carcinoma. Anogenital warts (condoloma acuminata) is caused by a number of different HPVs. The literature contains reports of progression of some of these lesions to locally invasive squamous cell carcinomas (Zur Hausen, H., *Curr. Top. Microbiol. Immunol.*, 78: 1-30 (1977)). Further, HPV-specific antigens have been detected in 50% of the cervical lesions interpreted as dysplastic. The clear epidemiologic association of cervical dysplasia to carcinoma in situ and invasive cervical carcinoma strongly suggests the role of at least HPV in this progression.

The existence of a large number of PVs, with more than one PV occurring in certain PV-induced lesions, the close association of papilloma and various carcinomas, as well as the non-cancer related medical problems resulting from virus-induced papillomas has produced an on-going ever-increasing need for a methodology to identify, with a high degree of certainty, the specific etiology of the papilloma. Thus, a need has continued to exist for a means for differentiating between the large number of PV types known to exist, as well as a means for further identifying as yet unknown PV types.

At the same time, it would be of substantial value, and a need has continued to exist, for the determination of the highly conserved nucleotide sequence which is common to all PVs and the "common antigen" which this highly conserved nucleotide sequence codes for. The determination of this sequence would be of substantial value in the production of antibodies which are cross-reactive with all PVs.

It is now known that productive papillomavirus infection of epithelial cells results in hyperplasia of cells in the spinous layer (acanthosis). Cells show an increase in size and in the number of desmosomes and tonofibrils. Other epithelial cells show degenerative changes with loss of tonofibrils, detachment of desmosomes, nuclear wrinkling, and cytoplasmic vacuolization. In the upper layers of the epithelium, these changes are more pronounced. Cells in the granular layer show nuclear degeneration, margination, and condensation of chromatin. Virions are evident in nuclei of degenerated cells in the keratin layer by electron microscopy and the frequently intercrystalline array.

Host immune responses to papillomavirus infection are not well understood but infection usually occurs in the young, followed by persistence of the wart for a variable period of time. After regression, the host is left immune to reinfection by the same virus. In humans, antibody response to HPV infection is characterized by the appearance of IgM prior to the onset of regression. Just subsequent to regression, both IgM and IgG antibodies are present; long after regression, only IgG is detectable (von Krough, G. J., *Dermatol.*, 18: 195-204 (1979)). This conversion from IgM to IgG has been observed in cattle experimentally infected with BPV as well (Lee, K. P. et al., *Cancer Res.*, 29: 1393-1397 (1969)).

It would appear that rejection of papillomas is closely associated with cell-mediated immunity. In cattle experimentally infected with papillomavirus, regression is preceded by infiltration of mononuclear leukocytes, mainly lymphocytes. This occurs generally in perivascular areas, but also as a diffuse scattering throughout the papilloma (Lee, K. P. et al., *J. Invest. Dermatol.*, 52: 454-464 (1969)).

In humans, regressing flat warts demonstrate a similar histological appearance with perivascular infiltration of mononuclear leukocytes in the upper dermis, with epidermal invasion sharply confined to the papilloma (Tagami, H. et al., *J. Dermatol.*, 90: 147-154 (1974)). This simultaneous regression of multiple warts at distant sites suggest that cell-mediated immunity plays a major role in papilloma rejection. Regression of flat warts, however, has no effect on plantar or palmar warts in the same individual, indicating that regression is HPV type-specific (Berman, A. et al., *Br. J. Dermatol.*, 99: 179-18 (1978)). A similar differential regression of warts has also been observed in cattle infected with multiple BPV types (Barthold, S. W. et al., *J. Am. Vet. Med. Assoc.*, 165: 276-280 (1974)).

SUMMARY OF THE INVENTION

In order to develop an assay for identifying specific PVs, it would be desirable to produce anti-sera to specific PVs, from which competitive and/or immunometric assays could be developed. For certain papillomaviruses such as HPV-1, one can prepare type-specific antigen or antibody because of the high amount of viral material present in plantar warts and the fact that no HPV DNA has been identified that will cross-hybridize to HPV-1 DNA under stringent conditions. However, for those viruses infecting mucosal epithelium, it is very difficult to obtain sufficient quantities of the viral particles to use as immunogenic materials. Because of the common antigenic determinants shown to be present on the capsid protein (presumably the interior), polyclonal antibodies would most likely result in cross-reactivity with other PVs.

Faced with the ongoing need for an assay to distinguish between the various PVs known to exist, the inventors originally conceived that a type-specific antigenically-determinative region in the capsid protein could be deduced from a computerized analysis of the DNA sequence coding for the major capsid protein of each PV. Use of molecular cloning techniques made sufficient quantities of the DNA available for sequencing.

That conception has led to the present invention, the discovery that the DNA sequence of the open reading frame encoding the major PV capsid protein (L1) of a given type does, in fact, contain at least one DNA segment which exhibits substantially no identity to its corresponding segment in any other PV type, and that this non-identical DNA sequence may be utilized in the preparation of PV type-specific DNA probes, oligopeptides for imparting type-specific immunogenic and/or immunologic properties, labelled oligopeptides, labelled antibodies, substantially pure antibodies, diagnostic methods, assay kits, and vaccines.

A similar analysis has led to another aspect of the present invention, the discovery of the highly conserved DNA sequence, within the sequence coding for the major capsid protein L1, which codes for the common PV antigen(s). This antigen (polypeptide) elicits the formation of antibodies which are crossreactive with any and all PVs. The discovery of this highly conserved nucleotide sequence makes possible the preparation of PV genus-specific antibodies, oligopeptides for imparting genus-specific immunogenic and immunologic properties, labelled genus-specific antibodies, diagnostic methods, assay kits, and the like.

BRIEF DESCRIPTION OF THE DRAWINGS

FIG. 2 shows the amino acid sequence of the L1 reading frames for BPV-1 and DPV.

FIG. 3 shows the amino acid sequence of the L1 reading frames for BPV-1, DPV and a portion of BPV-2.

FIG. 4 shows the aligned amino acid sequences of the L1 reading frames for BPV-1, DPV, HPV-1a, HPV-6b, CRPV and a portion of BPV-2. Homologous marking regions A, B, C, D and E, as well as preferred and more preferred type-specific (TS) regions, are shown.

DESCRIPTION OF THE PREFERRED EMBODIMENTS

The invention is applicable for any PV. One need merely obtain the nucleotide sequence for the L1 reading frame of the major capsid protein, utilizing sequencing techniques conventional and well known in the art, i.e. Maxam and Gilbert (1977), incorporated by reference. The first ATG codon is considered the first amino acid. Comparison with already known PV sequences, especially with those type-specific sequences indicated hereinbelow, or matching common, homologous regions utilizing, for example, computerized comparisons, will readily permit the identification of the variable regions within the nucleotide sequence, those regions capable of conferring PV-type specificity.

Having thus located the PV-type specific variable region within the DNA sequence, one may then (1) utilize the DNA sequence itself, in labelled form, as a type-specific probe; (2) utilize peptide sequences derivable from the DNA sequence, in labelled form, in PV-type specific competitive assays; (3) prepare substantially pure antibodies which are PV-type specific from peptide sequences derivable from the DNA sequence; (4) prepare labelled PV-type specific antibodies for immunometric assays; (5) prepare amino acid sequences for imparting PV-type specific immunogenic properties; and (6) prepare PV-type specific vaccines from the PV-type specific amino acid fragments. In short, any and all utilities disclosed for the typespecific variable region nucleotide sequences specifically taught herein are now available to those with ordinary skill in the art as a result of this invention, the techniques and concepts transferrable to all PVs.

For example, shown in FIG. 1 is a comparison of the L1 nucleotide sequence of three unrelated viruses, BPV-1, HPV-1 *a* and HPV-6*b*, by computer analysis using a hash matrix algorithm. FIG. 1 indicates that there are regions with significant degrees of sequence homology. The diagonal represents the regions of homology within the L1 reading frame. The degree of homology for each data point along with the diagonal is represented in the bar graph below each panel. Panel A is a comparison of BPV-1 (X-axis) versus HPV-1*a*; Panel B is a comparison of BPV-1 (X-axis) and HPV-6*b;* and Panel C is a comparison between HPV-6*b* (X-axis) and HPV-1*a*.

When the amino acid sequence of the L1 reading frames for BPV-1 and DPV are compared, there is exhibited a higher degree of identity than would be shown for the L1 polynucleotide sequence because of the redundancy of the genetic code (FIG. 2). Amino acid sequences were determined by translation of the nucleotide sequence of the L1 open reading frame. The amino acids are represented in the single letter code (see Lehninger, A. L., *Biochemistry*, 2nd Ed., page 72 (1975)) and the polypeptide sequences are numbered from the first methionine residue. The BPV-1 sequence is all uppercase and where a mismatch is encountered on the DPV sequence the amino acid is in lowercase. Gaps in the sequences were introduced for the purposes of alignment. Identity is scored as a vertical line between the two corresponding residues.

In FIG. 3, two viruses which share about 10% DNA sequence homology (liquid phase hybridization) and which are antigenically cross-reactive (albeit very weak) are compared, BPV-1 and DPV; the degree of amino acid identity is extremely high, except in five regions. Those regions on the BPV-1 amino acid sequence (numbered from the first methionine residue of the L1 reading frame) greater than 6 amino acids in length which do not show substantial identity to the DPV amino acid sequence are from positions 27 to 31, 46 to 57, 260 to 281, 342 to 348, and 465 to 484 and represent potential type-specifying domains. When the BPV-1 amino acid sequence is compared to the partial BPV-2 amino acid sequence, there is almost complete identity in the regions bounded by amino acids from positions 342 to 348 and 464 to 495, leaving a region between positions 262 to 283 which shows a substantial divergence in the amino acid identity exhibited between these two closely related viruses. In FIG. 3, amino acid sequences were determined by translation of the nucleotide sequence of the L1 open reading frame. The amino acids are represented in the single letter code and the polypeptide sequences are numbered from the first methionine residue. The BPV-1 sequence is all uppercase and where a mismatch is encountered on the BPV-2 or DPV sequence, the amino acid is in lowercase. Gaps in the sequences were introduced for the purposes of alignment. "∧" indicates the region of the BPV-2 L1 nucleotide sequence which is unknown. Identity is scored as a vertical line between the two corresponding residues.

FIG. 4 shows the amino acid sequence of the L1 reading frame for BPV-1, DPV, HPV-1*a*, HPV-6*b*, CRPV and a portion of BPV-2. Amino acid sequences were determined by translation of the nucleotide sequence of the respective L1 open reading frame. The amino acids are represented in the single letter code and each sequence is numbered from the first methionine residue. Amino acids are in uppercase if two or more show identity; lowercase amino acids indicate no identity. Gaps have been introduced for purposes of alignment. "∧" indicates the region of the BPV-2 nucleotide sequence which is unknown. "—" indicates where at least two amino acids are the same and "*" indicates that all of the amino acids are the same.

To confirm the conception that the domain bounded by amino acid positions (inclusive) 262 to 283 of the BPV-1 L1 reading frame could represent a type-specific immunogen, a decapeptide found between amino acid positions 274 and 283 was synthesized and antibodies raised against it. The decapeptide derived from the BPV-1 L1 sequence has the sequence (from the N-terminus) of:

lys-asn-asn-lys-gly-asp-ala-thr-leu-lys.

This sequence, using the single letter code is:

KNNKGDATLK.

The complete details of the procedure for raising antibodies against the synthesized polypeptide, as well as the results therefrom, are reported in Example 1 below. The hyperimmune sera to intact BPV-1 from rabbit was found to cross-react with BPV-1; it was also found to react with BPV-2 at about a 10-fold lower dilution. The antibody raised against the decapeptide did not react with BPV-2 fibropapillomas even at a dilution of 1:2 whereas it reacted at a 1:50 dilution with BPV-1 fibropapillomas. The results strongly indicate that antibodies to the decapeptide are BPV-1 type-specific; more importantly, this type-specific antibody can distinguish between two viruses (BPV-1 and BPV-2) which have been used to define the division between papilloma virus type and subtype, i.e. greater than or less than 50% DNA sequence homology. The BPV-1 virus and BPV-2 virus have 50% DNA sequence homology.

One aspect of the present invention is directed to the discovery of certain nucleotide sequences in the L1 reading frame which are themselves type-specific and which code for relatively small amino acid sequences which are type-specific as well. These isolated sequences have utility in their own right, i.e. in labelled form for DNA hybridization analysis. The term "isolated sequence" is meant to include DNA fragments which are not naturally occurring as fragments and would not be found in the natural state. These sequences are typically 5 to 75 nucleotides in length, preferably a minimum of 18 nucleotides long.

Figure 1A:
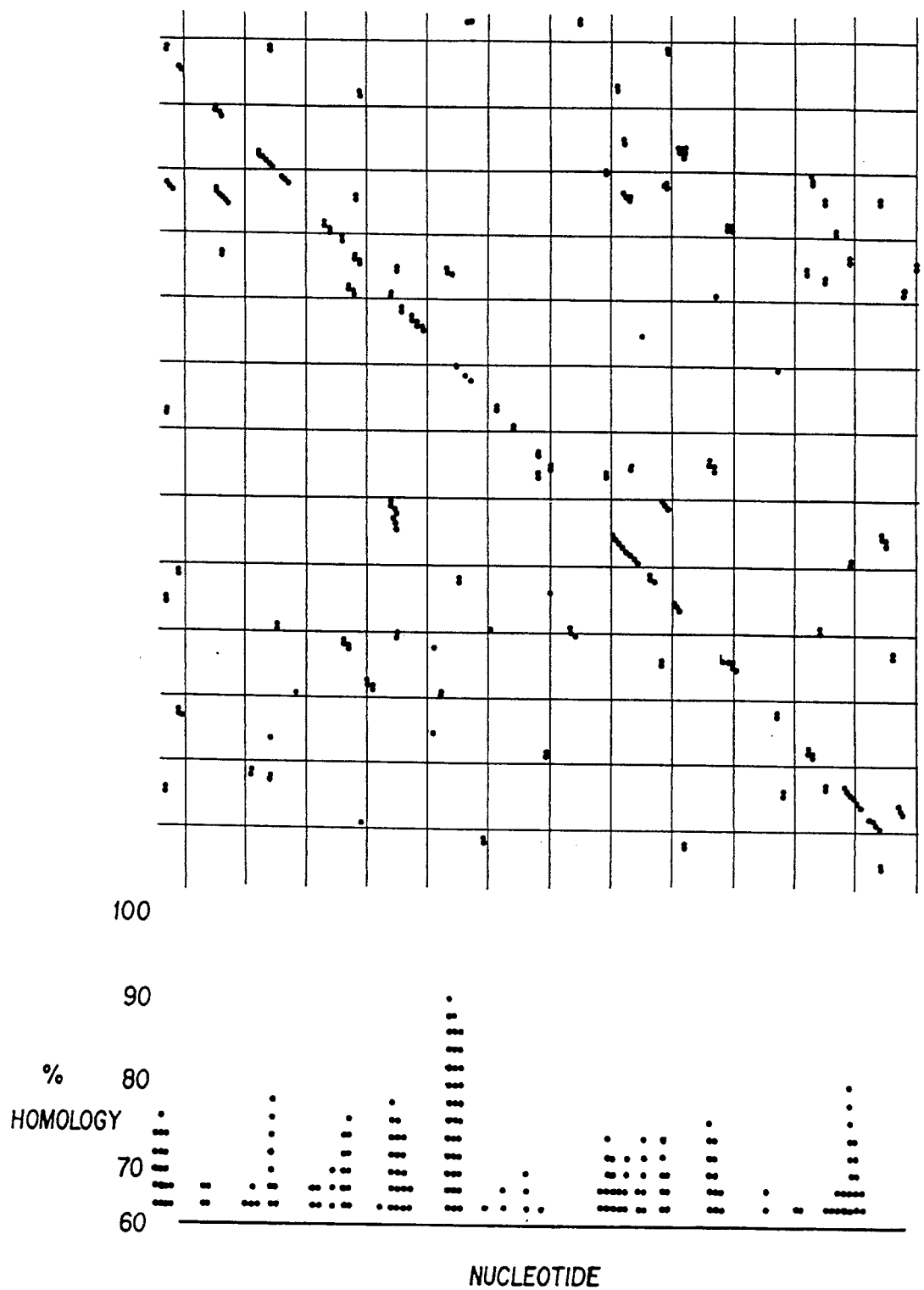
FIG. 1A-C shows the DNA sequence homology comparison of the L1 open reading frames of BPV-1, HPV-1a, and HPV-6b.
Figure 1B:
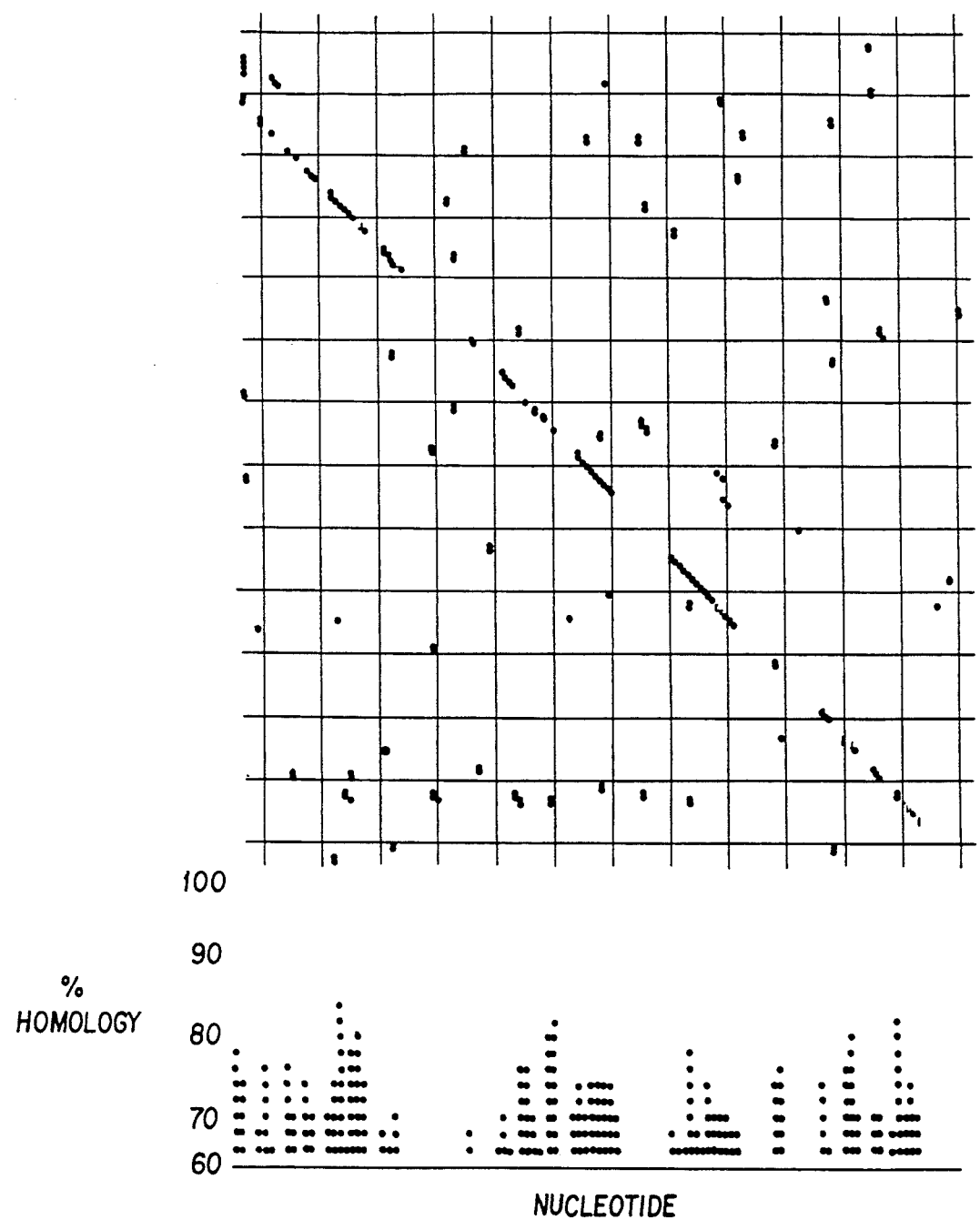
Figure 1C:
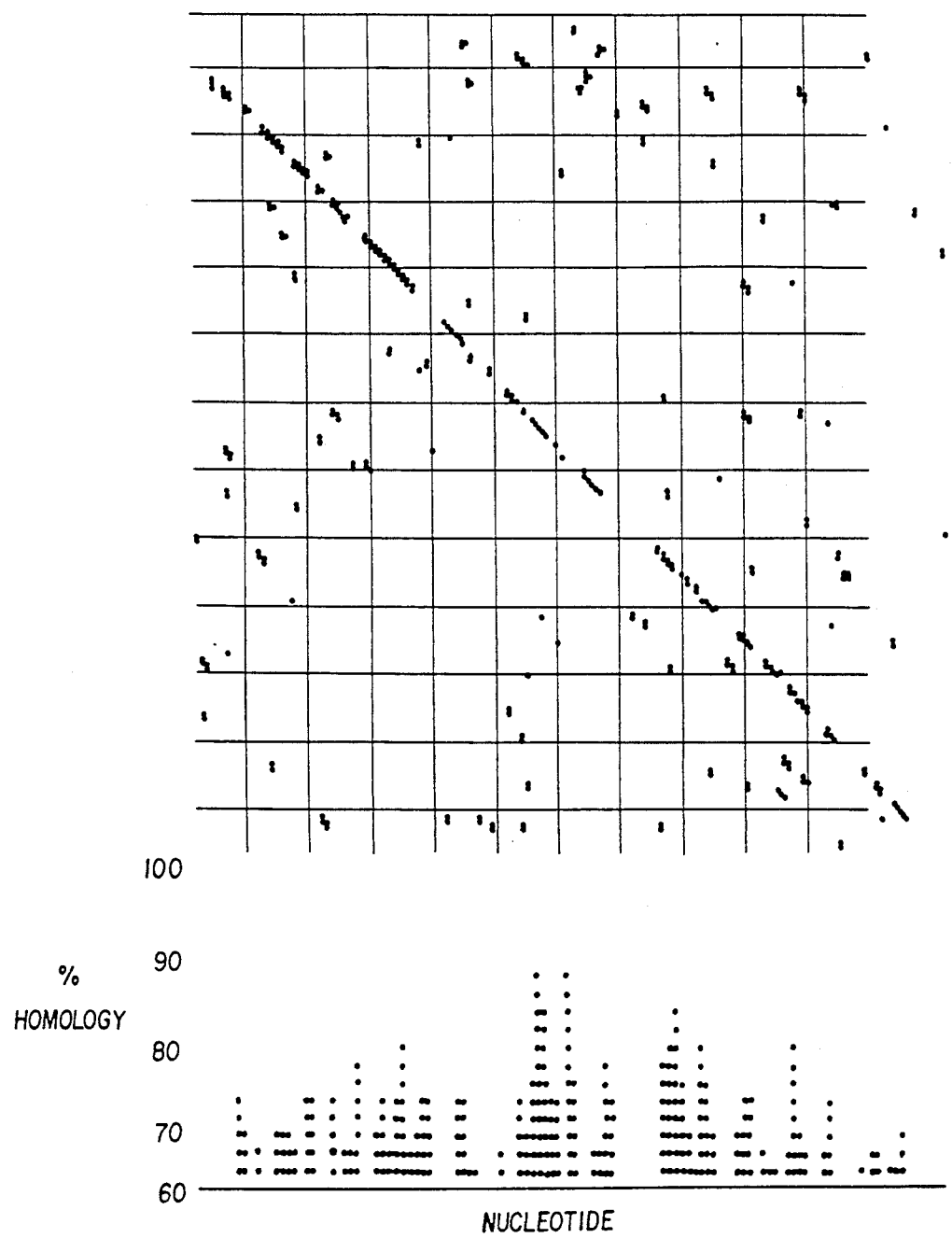
Figure 5:
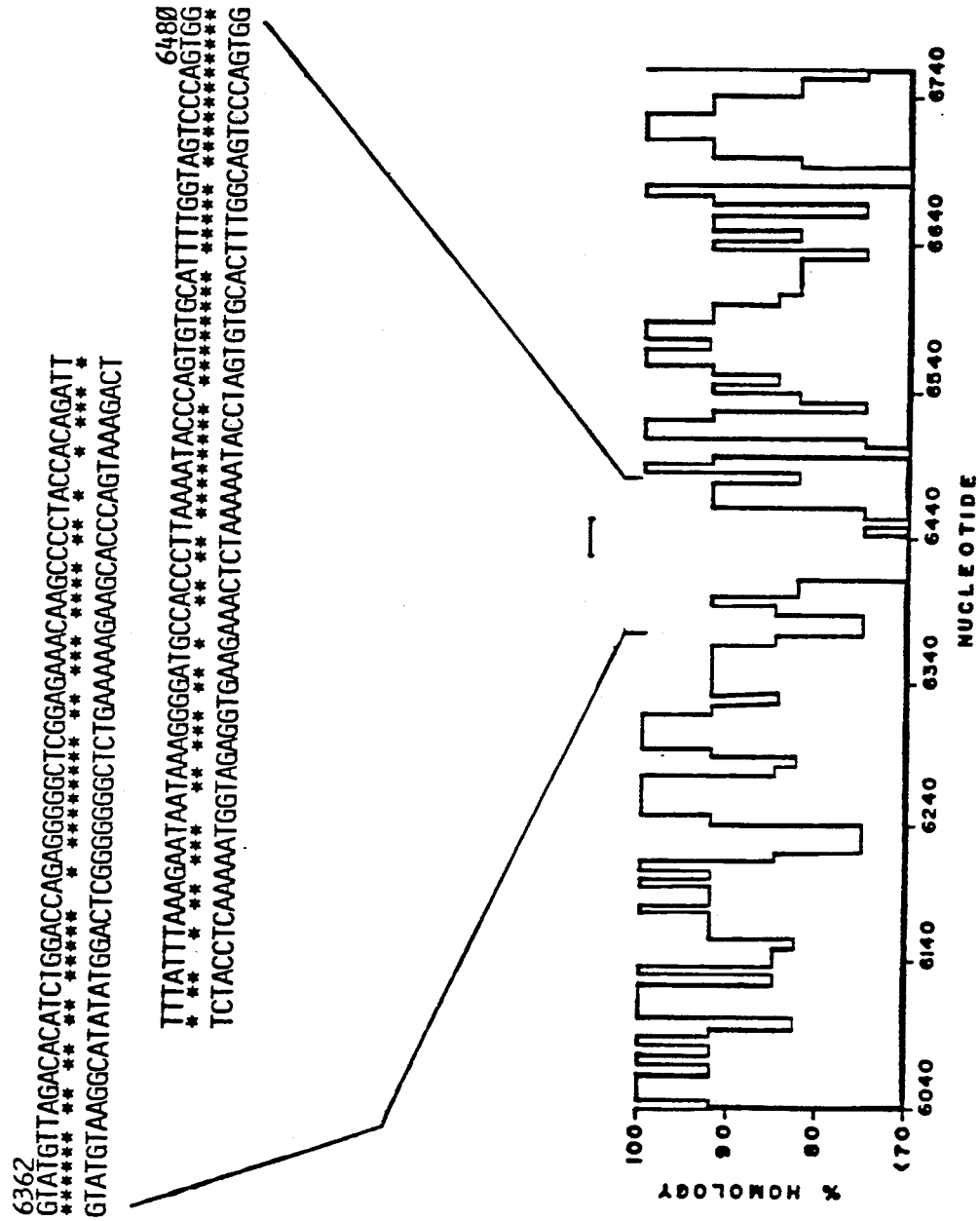
FIG. 5 is a comparison of DNA sequence homology between nucleotide 6040 and 6754 of the BPV-1 genome and BPV-2 genome.

FIG. 5 shows a comparison of DNA sequence homology between nucleotide 6040 and nucleotide 6754 of the BPV-1 genome and BPV-2 genome. The bar graph represents the degree of homology between the viral genomes with a region just upstream from position 6440 exhibiting the lowest degree of sequence homology. The upper nucleotide sequence shows the extent of homology within this region. Identical nucleotides are scored with "*". This region of low sequence homology represents the region of the L1 open reading frame in which there is amino acid divergence. The bar indicates the region encoding the polypeptide which was synthesized and used to raise BPV-1 type-specific antibodies.

Numbering from the first methionine residue, the region of greatest interest in the L1 open reading frame is from amino acid positions 262 to 283 for BPV-1 (22 amino acids; 66 nucleotides); amino acid positions 263 to 283 for DPV (21 amino acids; 63 nucleotides); amino acid positions 271 to 294 to HPV-1a (24 amino acids; 72 nucleotides); amino acid positions 266 to 290 for cottontail rabbit papillomavirus (CRPV) (25 amino acids; 75 nucleotides); amino acid positions 263 to 283 for HPV-6b (21 amino acids; 63 nucleotides) and amino acid positions 262 to 283 for BPV-2 (22 amino acids; 66 nucleotides). The nucleotide sequence for this region for each virus is given below:

BPV-1
TCGGAGAAACAAGCCCCTACCACAGATTTT-TATTTAAAGAATAATAAAGGGGAT GCCACCCTTAAA

DPV
ACTGACAAAGAACTCCCACCCGAGGCCTAT-TATCTGAAGCCACCGGGGGAGATG GAACTCAAA

HPV-1a
TCGTTGGGTGATAGGGAGGCAGTC-CCACAAAGCTTGTATTTAACAG-CAGATGCT GAACCAAGAACAACTTTA

CRPV
GGGGACAAGGAAAATGTGAAGAG-CAGGGCCTACATAAAACGCACACAGATG-CAG GGAGAGGCAAATGCCAACATT

HPV-6b
GAGGTGGGGGAACCTGTGCCTGATACACT-TATAATTAAGGGTAGTGGAAATCGC ACGTCTGTA

BPV-2
TCTGAAAAAGAAGCACCCAGTAAAGACTT-CTACCTCAAAAATGGTAGAGGTGAA GAAACTCTAAAA

This type-specifying region of DNA codes for a type-specific amino acid sequence, a polypeptide which is a relatively small sequence of amino acids within the amino acid sequence making up the major capsid protein. For the present invention, the terms "relatively small type-specific amino acid sequence" and "relatively small fragment" include an amino acid sequence which will render immunogenic and/or immunologic specificity to the peptide. As such, the peptide contains a minimum of 6 amino acids, and may include up to about three naturally occurring flanking amino acids on each side, with the proviso that the naturally occurring non-specific flanking amino acids must not be present in such numbers as to render the peptide cross-reactive with atypical (of a different type) PVs. As an upper limit on the amino acid sequence, 15 to 25 amino acid residues are included in the present invention. Again, however, the polypeptide must be immunospecific to fall within the invention.

By the terms "type-specific polypeptide" and "a polypeptide having a sequence of amino acids specific for a particular PV" is meant to include the polypeptides which correspond to the L1 capsid protein and confer type-specificity ("type-specific" and "typespecificity" defined as above). The polypeptides of the present invention correspond to the amino acid sequence bound preferably by residues 251 to 291, most preferably by residues 262 and 283 of the L1 capsid protein of BPV-1. The term includes both naturally occurring polypeptides, synthetic polypeptides which are homologous to the naturally occurring polypeptides and derivatives thereof. By "derivatives thereof" is meant those polypeptides which vary from the natural sequence but still confer type-specificity.

Further, this invention also includes synthetic peptides which have been synthesized to contain sufficient residues from within the type-specifying region to confer type-specific immunogenic and/or immunologic properties and further containing other residues not a part of the natural sequence.

The relatively small type-specific amino acid segment of the present invention may be utilized, for example, to prepare type-specific PV antisera, utilizing techniques described in Example 1 below. However, the present invention is in no way limited in the manner by which antisera and antibodies are prepared, this invention encompassing techniques already known or yet to be determined which involve antibody production from isolated antigen.

As above, the naturally occurring peptide segments contain sufficient amounts of the amino acids in the variable region to confer type-specificity, but may contain up to three flanking amino acids on each side of the variable regions.

As is understood by those skilled in the art, it is necessary at times to interpose spaces in the amino acid sequences in order to properly align the sequences.

In aligning the amino acid sequences, use is made of specific areas within the individual sequences which show exact homology to the corresponding residue locations in each sequence. Utilizing the BPV-1 (FIG. 4) amino acid sequence as the base sequence for numerical reference purposes, and referring again to FIG. 4, it may readily be seen that there are five regions within the amino acid sequence for all six papillomaviruses which show exact sequence homology. These regions are—including the extremes—between residues 105 and 110 (a six-amino acid sequence, RGQPLG, hereinafter region A), between residues 193 and 196 (a four-amino acid sequence, DGDM, hereinafter region B), between residues 200 and 203 (a four-amino acid sequence, GFGA, hereinafter region C), between residues 227 and 230 (a four-amino acid sequence, YPDY, hereinafter region D), and residues 292 and 295 (a four-amino acid sequence, PSGS, hereinafter region E).

As may be seen from FIG. 4, aligning the amino acid sequences for the major capsid protein of each of the PVs shown therein (determined by sequencing the polynucleotide of each) results in one area which is particularly devoid of sequence homology, the area between residues corresponding to BPV-1 residues 251 to 291, preferably 262 to 283. By particular attention to coinciding the tetrapeptide of region D and the tetrapeptide of region E, and coinciding amino acid residues bounded by regions D and E, where possible, the spacings demonstrated in FIG. 4 were (and can be) determined. In this manner, the type-specific sequences for any PV can be readily determined.

As has been shown above for BPV-1, the amino acid sequence of PV which corresponds to positions 251-291, preferably 262 to 283, including the extremes, define the region of type-specificity within the L1 capsid protein of PV. Equally, the corresponding region within the polynucleotide sequence which codes for the L1 capsid protein defines that region of DNA which is type-specific.

Given the above, and as indicated, one may now readily determine the type-specifying DNA sequence (and amino acid sequence) for any PV. One need merely sequence the DNA for the gene coding for the major capsid protein, deduce the amino acid sequence for the protein therefrom, align the sequence with a known sequence such as BPV-1 (making particular use of the "marking sequences", regions A-E) and select the DNA segment (or corresponding amino acid segment) which corresponds to amino acid residues 251-291, preferably 262-283 of the BPV-1 amino acid sequence.

For purposes of the present invention, the terms "type-specific papillomavirus DNA" or "polynucleotide sequence specific for a given papillomavirus type" is meant to include the polynucleotide which codes for the type-specific portion of the major capsid protein corresponding to residues 251-291, preferably 262-283 of the BPV-1 amino acid sequence or any derivative of that amino acid sequence, provided that the derivatives demonstrate type-specificity as well. As is understood by those skilled in the art, the terms include the naturally occurring sequences, synthetic sequences which are deduced from the natural sequences, sequences which are degenerate as a result of the genetic code, and those sequences which are variations due to the flexibility in the third base due to the "wobble" (See Watson, J. D. et al., *Recombinant DNA: A Short Course,* p. 38 (1983), Freeman and Company, New York, hereinafter "wobble derivatives."

Further included within the terms are those DNA sequences which include sufficient nucleotides within the designated polynucleotide sequence to confer type-specificity, i.e. sequences which overlap at one or the other end, thereby representing "type-specifying fragments" of the PV genome.

The polynucleotides of this invention which are "type-specific" or which demonstrate "type-specificity" include those polynucleotides demonstrating the ability to distinguish, using conventional hybridization techniques, between PV types, those PVs having less than 50% DNA sequence homology.

Specific polynucleotides within the present invention include those polynucleotides as set out above and which code for polypeptides which correspond to positions 251 to 291, preferably 262 to 283 on the BPV-1 sequence, degenerates as a result of the genetic code, and variations thereon due to the "wobble."

In a different embodiment of the present invention, it has also been discovered that a specific polynucleotide segment in the DNA coding for the major capsid protein of papillomavirus codes for a polypeptide which is the "common antigen" for papillomavirus.

Utilizing the same methodology described above for the "type-specific" polynucleotides and polypeptides, wherein BPV-1 represents the base amino acid sequence, for numbering purposes, it has now been determined that the amino acid sequence of all PVs which corresponds to the hexapeptide between residues 105 and 112, identified above as marking region A, is homologous. This six-amino acid sequence coded for thereby represents the "common antigen," i.e. it will generate antibodies which are genus-specific. These genus-specific antibodies are cross-reactive with all PVs and are useful in a variety of immunoassays. The labelled peptide sequence, and its derivatives, are also useful for immunoassays. In short, the same utilities contemplated for the type-specific polypeptide, are contemplated for the genus-specific polypeptides as well, i.e. labelled antibodies, assay kits, etc. In similar fashion, a six mer peptide which contains the homologous regions selected from B, C, D, E or other "common" region is also within the scope of this invention.

As may be seen from FIG. 4, one embodiment of this aspect of the invention comprises the hexapeptide:

Arg-Gly-Gln-Pro-Leu-Gly

As will be readily understood by those skilled in the art, included as well are the genus-specific polynucleotides coding therefor. By "derivatives" is meant those amino acid sequences which differ from the corresponding naturally occurring polypeptides in a manner such that the genus-specific nature of the sequence is unaltered.

IMMUNOASSAYS

In one embodiment, the antibodies raised against type-specific and genus-specific amino acid sequences of the major capsid proteins may be detectably labelled, utilizing conventional labelling techniques well-known to the art. Thus, the antibodies may be radiolabelled using, for example, radioactive isotopes such as $^{3}H$, $^{125}I$, $^{131}I$ and $^{35}S$.

In similar fashion, the peptide sequence may itself be detectably labelled, e.g. with a radioactive isotope.

The type-specific or genus-specific antibody or the peptide sequence antigen, genus- or type-specific, may also be labelled using fluorescent labels, enzyme labels, free radical labels, or bacteriophage labels, using techniques known to the art (Chard, supra).

Typical fluorescent labels include fluorescein isothiocyanate, rhodamine, phicoerythrin, phicocyanin, alophicocyanin, and Texas Red.

Since specific enzymes may be coupled to other molecules by covalent links, the possibility also exists that they might be used as labels for the production of tracer materials. Suitable enzymes include alkaline phosphatase, beta-galactosidase, glucose-6-phosphate dehydrogenase, maleate dehydrogenase, and peroxidase. Two principal types of enzyme immunoassay are the enzyme-linked immunosorbent assay (ELISA), and the homogeneous enzyme immunoassay, also known as enzyme-multiplied immunoassay (EMIT, Cyva Corporation). In the ELISA system, separation may be achieved, e.g., by the use of antibodies coupled to a solid phase. The EMIT system depends on deactivation of the enzyme in the tracer-antibody complex; the activity can thus be measured without the need for a separation step.

Additionally, chemiluminescent compounds may be used as labels. Typical chemiluminescent compounds include luminol, isoluminol, aromatic acridinium esters, imidazoles, acridinium salts, and oxilate esters. Similarly, bioluminescent compounds may be utilized for labelling, the bioluminescent compounds including luciferin, luciferase, and aequorin.

Once labelled, the antigenic polypeptide, or antibody against same, may be employed to identify and quantify immunologic counterparts (antibody or antigenic polypeptide) utilizing techniques well-known to the art.

A good description of a radioimmune assay (RIA) may be found in *Laboratory Techniques in Biochemistry and Molecular Biology* by Work, T. S. et al., with particular reference to the chapter entitled "An Introduction to Radioimmune Assay and Related Techniques" by Chard, T., North Holland Publishing Company, New York, New York (1978), incorporated by reference herein.

A good description of general immunometric assays of various types can be found in the following U.S. Pat. Nos. 4,376,110 (David et al.) or 4,098,876 (Piasio).

A particularly interesting type of assay involves incubating a small sample of test fluid suspected of containing a PV virus with an insoluble disc coated with purified antibodies reactive with the PV type-specific antigen. If the PV type-specific antigen (the amino acid sequence) is present in the fluid, an immunochemical bond forms between the antigen and the immobilized antibody. After washing away any soluble materials, the insoluble disc is subjected to a second incubation, this time with an enzyme- or radio-tagged conjugate reagent. In the event antigen was present in the sample, a second immunochemical bond forms between the immobilized antigen on the disc and the tagged antibody. After another washing to remove any unbonded material, the disc is subjected to determination, for example, a third incubation with a substrate, which, under the catalytic influence of an immobilized enzyme, would undergo a chemical reaction to form a detectable end product. This end product can be present in the solution only if antigens were present in the sample, since otherwise no tag is immobilized, and the end product cannot be produced.

In addition, the materials for use in the assay of the invention are ideally suited for the preparation of a kit. Such a kit may comprise a carrier means being compartmentalized to receive in close confinement one or more container means such as vials, test tubes, and the like, each of said container means comprising one of the separate elements to be used in the method.

For example, one of said container means may comprise soluble, detectably labelled antibody in lyophilized form or in solution. Another container may contain insolubilized antibody. The carrier means may also contain, in addition, a plurality of containers, each of which comprises different, predetermined, known amounts of antigen. These latter containers can then be used to prepare a standard curve into which can be interpolated the results obtained from the sample containing the unknown amount of antigen.

DNA HYBRIDIZATION ASSAYS

Viral genomes, because of their uniqueness and limited complexity, lend themselves especially well to varied hybridization approaches. The techniques involve radiolabelling of nucleic acids used as probes, DNA-DNA and RNA-DNA hybridization with immobilized nucleic acids, cytohybridization, and methods of kinetic analysis of DNA-DNA and RNA-DNA hybridization in solution. Purity and specific radioactivity of the nucleic acids used as probes are crucial, in general, nucleic acids with high specific radioactivity.

The purity of the nucleic acid used as probe is a most critical element in specific hybridization. It is preferred to use virus harvested from extracellular fluids rather than from infected cells, especially where complementary RNA (cRNA) or complementary DNA (cDNA) are employed. Viruses harvested from cells carry along contaminated cellular DNA, the latter not always eliminated by DNase treatment. Thus, the first step is to procure virus which is highly purified by any method known to the art that conserves the integrity of the virions so that treatment with DNase will not cause fragmentation of the encapsulated genome. The extracted viral DNA should be rigorously purified at this point, the genome emerging from purification is largely unfragmented so that it can be separated from cellular nucleic acids on the basis of physical properties such as size, as well as density or super-coiled state. Following this, the highly purified genome is treated with endonucleases to fragment same, followed by isolation and recovery of the fragment containing the desired nucleotide sequence coding for the type-specific or genus-specific viral protein. Alternatively, a specified polynucleotide probe can be independently synthesized. Finally, the probe is detectably labelled, the labels of most utility being $^{3}H$, $^{32}P$, $^{125}I$, enzymes, biotin/avidin, or the like. A more complete discussion of nucleic acid hybridization technology may be found in Huang, E. S. et al., Vol. 6, pp. 457–497 (1977), incorporated by reference herein.

The polynucleotide or oligonucleotide probe may be labelled with an atom or inorganic radical, most commonly using radionuclides, but also perhaps heavy metals. In some situations, it may also be possible to employ an antibody which will bind specifically to the probe hybridized to the single-stranded DNA. Oligonucleotide probe technology is disclosed by Szostak, J. W. et al., *Meth. Enzymol.*, 68:419–428 (1979), incorporated by reference herein.

Most commonly, a radioactive label is employed, suitable radioactive labels including $^{32}P$, $^{3}H$, $^{14}C$ or the like. Any radioactive label may be employed which provides for an adequate signal and has sufficient half-life. Other labels include ligands, fluorescers, chemiluminescers, enzymes, antibodies, and the like.

The computer analysis of the nucleotide sequence of six unique PV types, BPV-1, DPV, HPV-1*a*, HPV-6*b*, CRPV and BPV-2 identified a nucleotide sequence which is entirely non-homologous and which codes for antigenically type-specific proteins. The sequences are as follows:

BPV-1
TCGGAGAAACAAGCCCCTACCACAGATTTT-
TATTTAAAGAATAATAAAGGGGAT
GCCACCCTTAAA
DPV
ACTGACAAAGAACTCCCACCCGAGGCCTAT-
TATCTGAAGCCACCGGGGGAGATG
GAACTCAAA
HPV-1*a*
TCGTTGGGTGATAGGGAGGCAGTC-
CCACAAAGCTTGTATTTAACAG-
CAGATGCT GAACCAAGAACAACTTTA
CRPV

GGGGACAAGGAAAATGTGAAGAG-
CAGGGCCTACATAAAACGCACACAGATG-
CAG GGAGAGGCAAATGCCAACATT

HPV-6b

GAGGTGGGGGAACCTGTGCCTGATACACT-
TATAATTAAGGGTAGTGGAAATCGC
ACGTCTGTA

BPV-2

TCTGAAAAAGAAGCACCCAGTAAAGACTT-
CTACCTCAAAAATGGTAGAGGTGAA
GAAACTCTAAAA

Utilizing known techniques for preparing labelled DNA probes, it is possible to construct type-specific DNA probes for hybridization purposes. Thus, one aspect of the present invention is directed to PV type-specific DNA sequences, which can be ascertained as a result of sequence analysis.

For the purposes of the present invention, the term "type-specific DNA sequence" is meant to include the highly variable region in the PV genome which codes for the immunologically specific major capsid structural protein. As such, the desired nucleotide sequence includes flanking naturally occurring nucleotides as well, with the proviso that these flanking nucleotides may not be present in such numbers as to alter the hybridization specificity of the DNA sequence. Typically, the DNA sequence contains at least 18 nucleotides. Further intended within the scope of this invention are any and all other nucleotides containing, as a minimum, 18 members and coding for immunologically specific structural proteins.

In addition to being useful for generation of the peptide sequences themselves, the type-specific DNA sequences of the PVs are also useful for preparing DNA probes, utilizing techniques well known in the art. Typical DNA probe preparation techniques are described by Maniatis, T., *Molecular Cloning*, Cold Spring Harbor Laboratory (1982). In one described technique, *E. coli* DNA polymerase I may be utilized to add nucleotide residues to the 3'-hydroxy terminus that is created when one strand of a double-stranded DNA molecule is nicked. In addition, the enzyme, by virtue of its 5' to 3' exonucleolytic activity, may remove nucleotides from the 5' side of the nick. The elimination of nucleotides from the 5' side and the sequential addition of nucleotides to the 3' side results in the formation of the nick (nick translation) along the DNA (Kelley et al., *J. Biol. Chem.*, 245: 39 (1970)). By replacing the preexisting nucleotides with highly radioactive nucleotides, it is possible to prepare labelled DNA with a specific activity well in excess of $10^8$ cpm/ug (Rigby, P. W. J. et al., *J. Mol. Biol.*, 113: 237 (1977)).

A number of techniques for molecular hybridization are used for the detection of viral DNA sequences in tissues; each has certain advantages and disadvantages. When large amounts of tissue are available, analysis of hybridization kinetics provides the opportunity to accurately quantitate the amount of viral DNA present, as well as to distinguish sequences that are closely related but not identical to the probe and determine the percent homology. Reactions are run under conditions of hybridization (Tm-25° C.) in which the rate of reassociation of the probe is optimal (Wetmur J. G. et al., *J. Mol. Biol*, 31: 349–370 (1968)). The kinetics of the reaction are second-order when the sequences in the tissue are identical to those of the probe; however, the reaction exhibits complex kinetics when probe sequences have partial homology to those in the tissue (Sharp, P. A. et al., *J. Mol. Biol.*, 86: 709–726 (1974)).

Typically, DNA can be isolated from tissue by sectioning on a cryostat and lysing the sections with a detergent such as SDS and a chelating agent such as EDTA, optionally with overnight digestion with proteinase K (50 ug/ml). Protein is removed by phenol and chloroform extractions, and nucleic acids are precipitated with ethanol. RNA is removed by treatment with heat-treated RNase A and the DNA re-extracted with phenol and chloroform. For kinetic studies, DNA solutions are sheared to a uniform single-stranded piece size (about 500 nucleotides) by sonication. Probe DNAs are labelled to high specific activity using either $^3$H-thymidine triphosphate or alpha-$^{32}$p-deoxynucleotide triphosphates by nick translation (Rigby et al., supra). The concentration of probe to cell DNA is determined by the sensitivity desired. To detect one papillomavirus genome per cell would require 1.3 pg of probe per ug of cell DNA (Gelb, L. D. et al., *J. Mol. Biol.*, 57: 129–145 (1971)). DNAs are mixed, denatured, brought to the appropriate salt concentration and temperature, and allowed to hybridize for various periods of time. The rate of reassociation can be determined by quantitating the amount of probe hybridized either by hydroxy apatite chromatography (Britten, R. J. et al., *Science*, 161: 529–540 (1968)) or S1 nuclease digestion (Sutton, W. D., *Biochim. Biophys. Acta*, 240: 522–531 (1971)).

A more flexible method of hybridization is the Southern blotting technique (Southern, E. N., *J. Mol. Biol*, 93: 503–517 (1975)). This technique offers variability in the stringency of the hybridization reaction, as well as determination of the state of the viral sequences in the specimen under analysis. Cell DNA (5–20 ug) can either be digested with restriction endonucleases or left undigested and electrophoresed through agarose gels. The DNA is denatured in situ with alkali, neutralized and transferred to a nitrocellulose membrane. To facilitate transfer of DNA in gels containing undigested or Fo I sequences, DNA is depurinated by treatment of the gel with diluted HCl prior to denaturation (Wahl, G. M. et al., *Proc. Natl. Acad. Sci.*, 76: 3683–3687 (1979)). After washing, the membrane is baked under vacuum for two hours at 80° C. and prehybridized in 10X Denhardts solution (0.2% each of Ficoll, bovine serum albumin, polyvinylpyrollidone) in 4X SSC (SSC=0.15M NaCl, 0.05M sodium citrate) containing 50 ug/ml sonicated and denatured salmon sperm DNA for four hours at 60° C. Stringent hybridization (Tm-25° C.) carried out in solution containing $1-5 \times 10^6$ count/min $^{32}$p-labelled nick-translated DNA (specific activity of $1-2 \times 10^8$ counts/m/ug DNA), 1M NaCl, 1X Denhardts, 0.15M TES [Tris (hydroxymethyl) methyl-2-aminoethane sulfonic acid], pH 7.5 with 50 ug/ml sonicated and denatured salmon sperm DNA in 50% formamide for 16–24 hours at 37° C. The membranes are washed extensively in 0.1X SSC at 52° C., air dried, and exposed to x-ray film. For non-stringent hybridization (Tm-43° C.), total cellular DNA results in background hybridization which interferes with the detection of HPV sequences. For these reactions, supernatant fractions are isolated by lysing tissue sections as described above, but prior to deproteinization, the viscous solutions are brought to 1M NaCl and kept at 4° C. overnight to precipitate high molecular weight sequences. The high and low molecular weight fractions are separated by centrifugation at 12,000×g for 20 minutes in the cold. The supernatant is deproteinized, and the DNA is precipitated and used for Southern analysis. Reactions are carried out as described above, except human lymphocyte DNA is used in place of salmon sperm DNA and hybridizations contain 30% formamide. Membranes are washed extensively in 4X SSC at 52° C., air dried and exposed to x-ray film. Since the papillomaviruses have conserved DNA sequences which can be detected under non-stringent hybridization conditions, the non-stringent hybridization is useful for identifying PV's but not type-specific PV's.

A major consideration associated with hybridization analysis of papillomaviruses is the degree of relatedness the probe has with the sequences present in the specimen under study. This is important with the Southern blotting technique, since a moderate degree of sequence homology under stringent conditions of hybridization can yield a strong signal even though the probe and sequences in the sample represent different virus types. HPV-6 and HPV-11 share about 25% sequence homology under stringent conditions (Gissman, L. et al., *J. Virol.*, 44: 393–400 (1982)) and, unless restriction enzyme analyses are performed, it is difficult to determine if a signal is due to HPV-6 or HPV-11 sequences. To distinguish these two virus types and their subtypes, Pst I digestion has proven useful (Gissman, L. et al., *Proc. Natl. Acad. Sci.*, 80: 560–563(1983)). An example of this cross-hybridization is shown in Example 2 below and FIG. 5.

The labelled probes, as described above, provide a general diagnostic method for detection of type-specific PVs. The method is reasonably rapid, has a simple protocol, has reagents which can be standardized and provided as commercial kits, and allows for rapid screening of large numbers of samples. In one method for carrying out the procedure, a clinical isolate containing genome is treated to provide single-stranded genomic nucleic acid, the single-stranded polynucleotide then fixed to a support. The affixed nucleic acid, DNA or RNA is contacted with a labelled polynucleotide having a base sequence complementary to the coding strand of the gene coding for the type specifying capsid protein.

The primary reagent is the labelled probe which may be RNA or DNA. In general, the probe will have at least about 25 bases, more usually at least about 30 bases, and may have even more than that. The limitation with this regard is that the probe not contain more than the minimum number of nucleotides required to maintain PV-type specificity with regard to the protein that it codes for.

Broadly, the probe may be obtained from messenger RNA, from cDNA obtained by reverse transcription of messenger RNA with reverse transcriptase or by cleavage of the genome, conveniently by endonuclease digestion, followed by cloning of the gene or gene fragment in accordance with known techniques. See, for example, Kornberg, *DNA Replication*, W. H. Freeman & Co., San Francisco, 1980, pp. 670–679. Alternatively, the gene may be synthesized according to the technique described by Merrifield, *J. M. Chem. Soc.*, 85:2149 (1962). After isolation of the DNA fragment, the fragment may be used for preparation of the probe.

The particular hybridization technique is not essential to the invention, any technique commonly used in the art being within the scope of the present invention. Typical probe technology is described in U.S. Pat. No. 4,358,535 to Falkow et al., incorporated by reference herein.

As with the immunoassays described above, the hybridization assays of the present invention are particularly well suited for presentation and commercialization in kit form, the kit comprising a carrier means compartmentalized to receive one or more container means (vial, test tube, etc.) in close confinement, each of said container means comprising one of the separate elements to be used in the hybridization assay.

For example, one vial may contain soluble, detectably labelled type-specific or genus-specific DNA sequence (a labelled probe), while one or more different vials may contain different, predetermined amounts of PV antigen. The latter containers may be used to construct a standard curve for interpolating data obtained from the unknown sample.

VACCINES

One aspect of the present invention involves the development of PV type-specific vaccines. There are various methods for preparing vaccines against viruses. The basic preferred requirements for any vaccine and for a method for the preparation of a vaccine are that (1) the resulting vaccine contain the necessary antigenic determinants to induce formation of antibodies in the host; (2) the vaccine possess high immunogenic potential; (3) the resulting vaccine be safe enough to be administered without any danger of clinical infection, either for the recipient or any contact of the recipient, and therefore, the risk associated with vaccination be minimized, if not totally eliminated; (4) the resulting vaccine be devoid of any toxic side-effects, for example, fever from endotoxin present in killed or extracted cells; (5) the resulting vaccine be suitable for administration by an effective route, for example, oral, intranasal, topical or parenteral; (6) the resulting vaccine mimic closely the circumstances of natural infection; (7) the resulting vaccine be stable under conditions of long-term storage, and that said long-term storage be at room temperature and (8) the resulting vaccine be compatible with the usual inert vaccine carriers. Those conditions can be achieved by the vaccines of the present invention.

In one embodiment of the present invention, vaccines prepared from immunogenically type-specific amino acid sequences of the L1 reading frame comprise the antigenic component of the vaccine. It may be necessary or preferable to covalently link the antigen to an immunogenic carrier, i.e. bovine serum albumin or keyhole limpet hemocyanin. The vaccines of the present invention may be administered to any mammal susceptible to infection with the papillomavirus. Human and non-human mammals may benefit as hosts.

Administration may be parenteral, but preferably oral or intranasal, depending upon the natural route of infection. The dosage administered may be dependent upon the age, health, weight, kind of concurrent treatment, if any, and nature of the papillomavirus. The vaccine may be employed in dosage forms such as capsules, liquid solutions, suspensions, or elixirs, for oral administration, or sterile liquid formulations such as solutions or suspensions for parenteral or intranasal use. An inert, immunologically acceptable carrier is preferably used, such as saline or phosphate-buffered saline.

The method of the present invention makes possible the preparation of vaccines against any PV for which the specific portion of the nucleic acid sequence coding for an immunogenically active peptide of the L1 capsid protein is known. Further, the same concept permits the preparation of vaccines from any immunogenic type specific nucleic acid sequence within the DNA of the PV.

Having now generally described the invention, the following examples are offered by way of illustration and are not intended to be limiting unless otherwise specified.

EXAMPLE 1

The decapeptide derived from portions 274 to 283 of the BPV-1 L1 sequence, lys-asn-asn-lys-gly-asp-ala-thr-leu-lys (from the N-terminus), was synthesized. Chromatographic analysis indicated purity of the decapeptide as being greater than 98%. The decapeptide was coupled to poly-DL-alanine-poly-L-lysine and this conjugate coupled to the adjuvant peptide N-acetylmuramyl-L-alanine-D-isoglutamine. The conjugate was homogenized in Freund's complete adjuvant. Rabbits were inoculated intramuscularly with the conjugated decapeptide, three injections of this preparation at two week intervals, followed by three additional injections at two week intervals with unconjugated decapeptide. Two weeks after the third conjugate injection, a very weak antibody response was detected by immunofluorescence on acetone-fixed frozen sections of BPV-1 fibropapillomas. After the third unconjugated peptide injection, the antibody response was detectable by immunofluorescence at a 1:50 dilution. In contrast, hyperimmune rabbit sera raised against intact BPV-1 has about a 10-fold higher titer assay by immunoflourescence. Although such hyperimmune sera reacted with BPV-1, it also reacted with BPV-2 containing fibropapillomas at about a 1:125 dilution. However, the antibody raised against the decapeptide did not react with BPV-2 fibropapillomas at a dilution of 1:2. These results indicate that antibodies to the decapeptide are BPV-1 type-specific.

Figure 6:
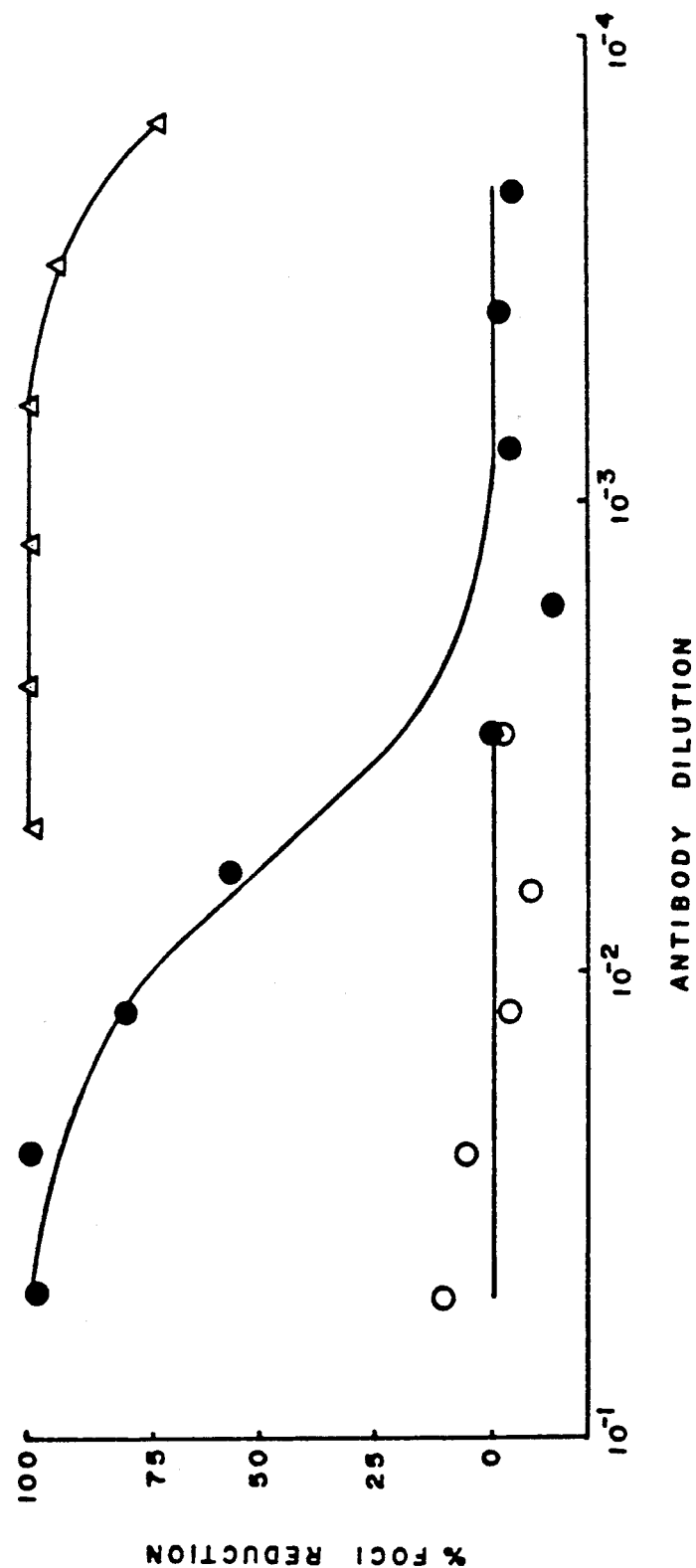
FIG. 6 demonstrates the kinetics of neutralization of BPV-1 transforming activity by antiserum against the type-specific decapeptide.

FIG. 6 shows the kinetics of neutralization of BPV-1 transforming activity by antiserum against the decapeptide. BPV-1 was incubated in the presence of either antiserum against the decapeptide ( ), antiserum against detergent-disrupted BPV-1 (Δ), or normal rabbit serum (○). Monolayers of C127 mouse cells were infected with serum-treated virus and focus formation scored after three weeks. Fifty percent neutralization of virus transforming activity for the antiserum against detergent-disrupted BPV-1 was about 1:10,000; normal rabbit serum failed to inhibit BPV-1 transforming activity.

Having now fully described the invention, it will be obvious to those with ordinary skill in the art that certain changes and modifications may be practiced within the scope of the appended claims.

What is claimed as new and desired to be covered by United States Letters Patent is:

1. A detectably labelled polynucleotide sequence comprising:
   a papillomavirus polynucleotide sequence useful in distinguishing between papillomavirus types wherein said papillomavirus sequence comprises at lest 15 nucleotides of a L1 open reading frame type-specific sequence, but less than the entire genome of said papillomavirus.

2. The detectably labelled polynucleotide sequence of claim 1, wherein said papillomavirus sequence comprises 15 to 75 nucleotides of said L1 open reading frame type-specific sequence.

3. The detectably labelled polynucleotide sequence of claim 2, wherein said papillomavirus sequence comprises 18–75 nucleotides of said L1 open reading frame type-specific sequence.

4. The detectably labelled polynucleotide sequence of claim 1, wherein said papillomavirus sequence comprises the nucleotide sequence of a given papillomavirus type which corresponds to BPV-1 L1 protein amino acids 251–291.

5. The detectably labelled polynucleotide sequence of claim 1, wherein said papillomavirus sequence comprises the nucleotide sequence of a given papillomavirus type which corresponds to BPV-1 amino acids 262–283.

6. An isolated polynucleotide segment comprising:
   a papillomavirus polynucleotide sequence useful in distinguishing between papillomavirus types wherein said papillomavirus sequence comprises at least 15 nucleotides of a L1 open reading frame type-specific sequence but less than the entire genome of said papillomavirus.

7. The isolated polynucleotide segment of claim 6, wherein said type-specific sequence comprises 15–75 nucleotides of said L1 open reading frame type-specific sequence.

8. The isolated polynucleotide segment of claim 6, wherein said papillomavirus sequence comprises the nucleotide sequence of a given papillomavirus type corresponding to BPV-1 L1 protein amino acids 251–291.

9. The isolated polynucleotide segment of claim 6, wherein said papillomavirus sequence comprises the nucleotide sequence of a given papillomavirus type corresponding to BPV-1 amino acids 262–283.

10. A method for characterizing a papillomavirus by type comprising:
    a) contacting a sample containing single-stranded papillomavirus DNA with a papillomavirus type-specific polynucleotide probe,
    wherein said probe comprises a papillomavirus type-specific sequence comprises 15–75 nucleotides of a L1 open reading frame type-specific sequence specific for a given papillomavirus type;
    b) allowing hybridization to proceed between said DNA and said probe;
    c) detecting the probe-DNA hybrids; and
    d) characterizing the type of said papillomavirus DNA by the presence of absence of said hybrids.

11. The method of claim 10, wherein said type-specific papillomavirus sequence comprises 18–75 nucleotides of said L1 open reading frame sequence.

12. The method of claim 10, wherein said probe is labelled.

13. The detectably labelled sequence of claim 1 wherein the label is selected from a radiolabel, a fluorescent label, a chemiluminescent label, an enzyme label, an antibody label and a free radical label.

14. The detectably Labelled polynucleotide sequence of claim 1 which comprises:

TCGGAGAAACAAGCCCCTAC-
    CACAGATTTTTATT-
    TAAAGAATAATAAAGGGGAT
    GCCACCCTTAAA, or a type-specific derivative thereof.

15. The detectably labeled polynucleotide sequence of claim 1 which comprises:

ACTGACAAAGAACTCCCACCCGAGGC-
    CTATTATCTGAAGCCACCGGG-
    GGAGATG GAACTCAAA, or a type-specific derivative thereof.

16. The detectably labelled polynucleotide sequence of claim 1 which comprises:

TCGTTGGGTGATAGGGAGGCAGTC-
CCACAAAGCTTGTATTTAACAG-
CAGATGCT GAACCAAGAACAACTTTA, or a type-specific derivative thereof.

17. The detectably labelled polynucleotide sequence of claim 1 which comprises:

GGGGACAAGAAAATGTGAAGAG-
CAGGGCCTACATAAAACG-
CACACAGATGCAG
GGAGAGGCAAATGCCAACATT, or a type-specific derivative thereof.

18. The detectably labelled polynucleotide sequence of claim 1 which comprises:

GAGGTGGGGGAACCTGTGCCT-
GATACACTTATAATTAAGGGTAGT-
GGAAATCGC ACGTCTGTA.

or a type-specific derivative thereof.

19. The detectably labelled polynucleotide sequence of claim 1 which comprises:

TCTGAAAAAGAAGCACCCAG-
TAAAGACTTCTACCTCAAAAATG-
GTAGAGGTGAA GAAACTCTAAAA, or a type-specific derivative thereof.

20. The isolated polynucleotide segment of claim 6 wherein said sequence comprises:

TCGGAGAAACAAGCCCCTAC-
CACAGATTTTTATT-
TAAAGAATAATAAAGGGGAT
GCCACCCTTAAA or a type-specific derivative thereof.

21. The isolated polynucleotide segment of claim 6 wherein the sequence comprises:

ACTGACAAAGAACTCCCACCCGAGGC-
CTATTATCTGAAGCCACCGGG-
GGAGATG GAACTCAAA or a type-specific derivative thereof.

22. The isolated polynucleotide segment of claim 6 wherein the sequence comprises:

TCGTTGGGTGATAGGGAGGCAGTC-
CCACAAAGCTTGTATTTAACAG-
CAGATGCT GAACCAAGAACAACTTTA or a type-specific derivative thereof.

23. The isolated polynucleotide segment of claim 6 wherein the sequence comprises:

GGGGACAAGGAAAATGTGAAGAG-
CAGGGCCTACATAAAACG-
CACACAGATGCAG
GGAGAGGCAAATGCCAACATT or a type-specific derivative thereof.

24. The isolated polynucleotide segment of claim 6 wherein the sequence comprises:

GAGGTGGGGGAACCTGTGCCT-
GATACACTTATAATTAAGGGTAGT-
GGAAATCGC ACGTCTGTA or a type-specific derivative thereof.

25. The isolated polynucleotide segment of claim 6 wherein the sequence comprises:

TCTGAAAAAGAAGCACCCAG-
TAAAGACTTCTACCTCAAAAATG-
GTAGAGGTGAA GAAACTCTAAAA or a type-specific derivative thereof.

26. The method of claim 10 wherein said polynucleotide probe is a papillomavirus L1 open reading frame type-specific labelled DNA probe.

27. The method of claim 10 wherein said polynucleotide probe is a papillomavirus L1 open reading frame type-specific labelled RNA probe.

28. The method of claim 12 wherein said probe is labelled with a member selected from the group consisting of radiolabel, enzyme label, antibody label, chemiluminescent label, fluorescent label and free radical label.

* * * * *